(12) United States Patent
Varghese et al.

(10) Patent No.: US 7,331,926 B2
(45) Date of Patent: *Feb. 19, 2008

(54) ULTRASONIC ELASTOGRAPHY PROVIDING AXIAL, ORTHOGONAL, AND SHEAR STRAIN

(75) Inventors: Tomy Varghese, Madison, WI (US); Udomchai Techavipoo, Madison, WI (US); Quan Chen, Madison, WI (US); James A. Zagzebski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 506 days.

This patent is subject to a terminal disclaimer.

(21) Appl. No.: 10/784,526

(22) Filed: Feb. 23, 2004

(65) Prior Publication Data

US 2005/0165309 A1 Jul. 28, 2005

Related U.S. Application Data

(63) Continuation-in-part of application No. 10/765,293, filed on Jan. 27, 2004.

(51) Int. Cl.
*A61B 8/00* (2006.01)
(52) U.S. Cl. .................................................. 600/443
(58) Field of Classification Search ................ 600/443, 600/447, 437–438; 128/916
See application file for complete search history.

(56) References Cited

U.S. PATENT DOCUMENTS

| | | | |
|---|---|---|---|
| 5,910,119 A | 6/1999 | Lin | |
| 5,997,480 A | 12/1999 | Sumanaweera et al. | |
| 6,193,665 B1 | 2/2001 | Hall et al. | |
| 6,241,675 B1 | 6/2001 | Smith et al. | |
| 6,687,625 B2* | 2/2004 | Srinivasan et al. | 702/42 |
| 2004/0234113 A1* | 11/2004 | Miga | 382/128 |
| 2005/0119568 A1* | 6/2005 | Salcudean et al. | 600/437 |

OTHER PUBLICATIONS

Elisa Konofagou, et al., A New Elastographic Method for Estimation and Imaging of Lateral Displacements, Lateral Strains, Corrected Axial Strains and Poisson's Ratios in Tissues, Ultrasound In Med. & Biol., Vo.. 24, No. 8, pp. 1183-1199, 1998, World Federation for Ultrasound in Medicine & Biology. Published in the USA.
Mark A. Lubinski, et al., Lateral Displacement Estimation Using Tissue Incompressibility, IEE Transactions on Ultrasonics, Ferroelectrics, and Frequency Control, vol. 43, No. 2, Mar. 1996.

* cited by examiner

*Primary Examiner*—Francis J. Jaworski
(74) *Attorney, Agent, or Firm*—Boyle Fredrickson S.C.

(57) ABSTRACT

Ultrasonic signals obtained at a range of angles are fit to a material independent model to derive both axial and lateral strain and thus parameters dependent on lateral strain including Poisson's ratio and shear strain.

32 Claims, 2 Drawing Sheets

ULTRASONIC ELASTOGRAPHY PROVIDING AXIAL, ORTHOGONAL, AND SHEAR STRAIN

CROSS-REFERENCE TO RELATED APPLICATIONS

This application is a continuation-in-part of U.S. application Ser. No. 10/765,293 filed Jan. 27, 2004.

STATEMENT REGARDING FEDERALLY SPONSORED RESEARCH OR DEVELOPMENT

This invention was made with United States government support awarded by the following agencies:
NIH CA86278
The United States has certain rights to this invention.

BACKGROUND OF THE INVENTION

The present invention relates to ultrasonic medical imaging and in particular to an apparatus and method for making ultrasonic elastography measurements.

Elastography is a new imaging modality that reveals the stiffness properties of tissue, for example, axial strain, lateral strain, Poisson's Ratio, Young's Modulus, and other common strain and strain-related measurements. The strain measurements may be collected over an area and compiled as a two-dimensional array of data, which may then be mapped to a gray or color scale to form a strain "image". Analogously, strain measurements may be collected over a volume displayed either three-dimensionally or as a series of stacked two-dimensional images.

In quasi-static elastography, two images of the tissue may be obtained by the ultrasound device in two different states of compression, for example, no compression and a given positive compression. The tissue may be compressed by an external agency such as a probe or the like, or may be compressed by muscular action or the movement of adjacent organs. Strain may be deduced from these two images by computing gradients of the relative local shifts or displacements in the images along the compression axis. Quasi-static elastography is analogous to a physician's palpation of tissue in which the physician determines stiffness by pressing the tissue and detecting the amount the tissue yields under this pressure.

In dynamic elastography, a low-frequency vibration is applied to the tissue and the tissue vibrations are measured, for example, using Doppler detection.

Typically quasi-static elastography produces a strain measurement only along the axis of compression. However, lateral strain or elevational strain (both perpendicular to the axial strain) may be of value both in deducing qualities like Poisson's Ratio and in countering the effects of lateral motion in de-correlating the axial displacement of the tissue. In addition, shear strain images can also be obtained.

A number of different methods have been used to obtain lateral strain in quasi-static elastography. Some of these techniques assume knowledge about the compressibility of the tissue (for example, Poisson's ratio), and thus cannot be used for measurements in which such tissue properties are to be determined. U.S. Pat. No. 6,270,459 to Ophir et al describes a technique which interpolates between successive axial rays or echo signals to provide a basis for horizontal displacement measurement using a correlation technique.

U.S. patent application Ser. No. 10/765,293 by the present inventors, entitled: "Ultrasonic Elastography With Angular Compounding" and hereby incorporated by reference, provides a method of obtaining both axial and lateral strain using multiple angles of ultrasonic measurement and an angle-dependent weighting factor based on an assumed value of the Poisson's ratio The compounding of the measurements from multiple angles improves the accuracy of the strain determinations.

SUMMARY OF THE INVENTION

The present invention provides an improved method of extracting axial, lateral, and elevational strain (more generally orthogonal strain tensor components) and displacements by developing a model representing projected displacements measured by ultrasound at multiple angles and as a function of axial and lateral displacement. The model is then fit to actual ultrasonic measurements and a noise-reduced estimation of axial and orthogonal displacements are extracted from the adjusted model. Axial and orthogonal displacements are then used to develop other parameters including axial and orthogonal strain, Poisson's ratio, and shear strains.

Importantly, the model does not need to presuppose the mechanical properties of the tissue (e.g., Poisson's ratio), and thus may be used in measurements of such mechanical properties. The fitting of the model and data provides a sophisticated method of reducing the effect of noise on any one measured value.

Specifically then, the present invention provides an ultrasonic elastography system including an ultrasonic acquisition assembly adapted to provide a set of ultrasonic signals from a plurality of voxels in a region of interest at a plurality of angles through the voxels, the set of ultrasonic signals including a first subset of ultrasonic signals taken with tissue of the region of interest in a first axial compressive state and a corresponding second subset of ultrasonic signals taken with tissue of the region of interest in a second axial compressive state. A processor receiving the set of ultrasonic signals, executes a stored program to: (i) measure the displacement of each voxel projected along the angle of each of the ultrasonic signals between the first and second compressive states; (ii) fit a model providing projected displacement as a function of ultrasonic signal angle and axial and orthogonal displacement to the measured displacements at each voxel; and (iii) determine axial and orthogonal displacement for the voxels from the fit model.

Thus one object of at least one embodiment of the invention is to provide an improved method and apparatus for extracting axial and orthogonal displacements from a multi-angled ultrasonic acquisition. The fitting of a model to multiple measurements reduces the effect of noise in any single measurement.

The processor may further determine parameters for the voxels related to the determined axial and orthogonal displacements.

It is yet another object of at least one embodiment of the invention to provide information about displacement related parameters such as Poisson's ratio, normal and sheer strains and stress distributions.

The model need not presuppose material properties of the voxels.

It is yet another object of one embodiment of the invention to provide a method that can be used to determine material properties of the voxels.

The plurality of angles of ultrasonic signals are in multiple perpendicular planes.

It is yet another object of at least one embodiment of the invention to provide for 3-dimensional displacement measurements and parameters derived from such measurements.

The ultrasonic acquisition assembly may include a transducer selected from the group consisting of: a single transducer element moved in location and angle, a multi-element transducer moved in location and angle, a phased array transducer sweeping in angle and moved in location, and beam steering on multielement transducers held stationary or moved in location.

It is yet another object of at least one embodiment of the invention to provide a method that flexibly works with a variety of different transducer designs.

The ultrasound elastography system may include a display device and the processor may provide an image output to the display based on the determined axial and orthogonal displacements, for example, an image based on axial and/or lateral strain, and/or elevational strain, and/or Poisson's ratio, and/or shear strain.

It is yet another object of at least one embodiment of the invention to provide a system that produces new views of tissue not normally obtained from ultrasonic equipment.

The foregoing objects and advantages may not apply to all embodiments of the inventions and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

DETAILED DESCRIPTION OF THE PREFERRED EMBODIMENT

Figure 1:
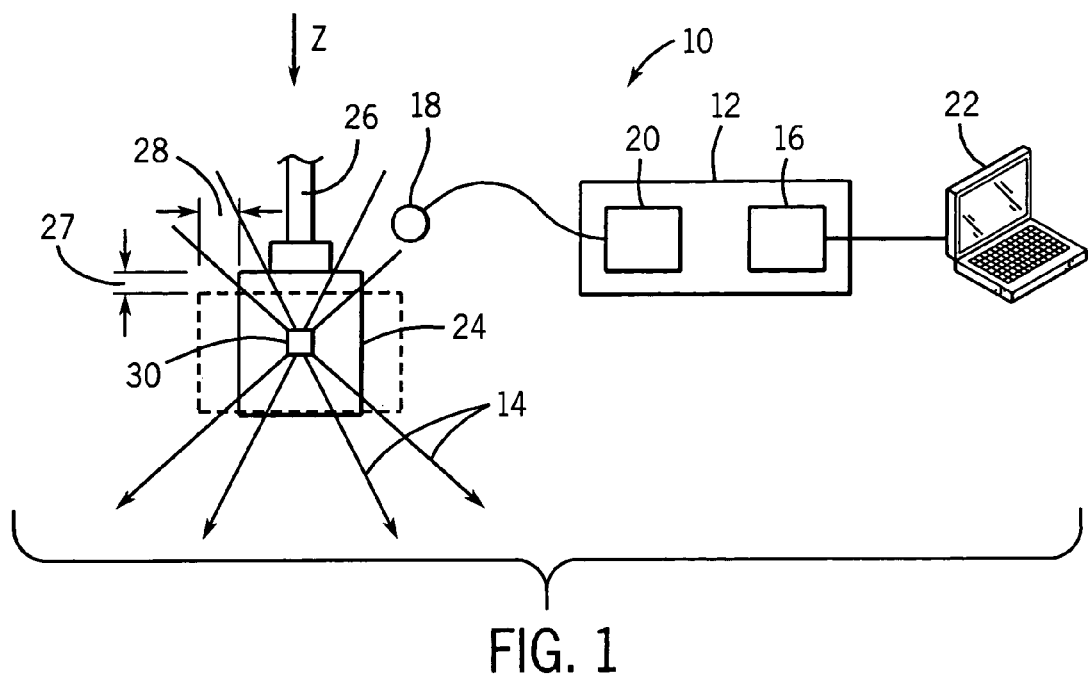
FIG. 1 is a simplified block diagram of an ultrasound machine suitable for acquiring multi-angle ultrasonic measurements used in the present invention.

Referring now to FIG. 1, an elastographic imaging system 10 suitable for use with the present invention may employ acquisition electronics 12, for example, a commercial ultrasonic imaging machine programmed according to the present invention, or a combination of such a machine and an external computer processing data acquired by the commercial machine.

Generally the acquisition electronics 12 includes an ultrasonic transducer 18, interface circuitry 20, and a processor 16 communicating with a terminal or display device 22. In operation, the transducer 18 provides ultrasound signals and position signals to the interface circuitry 20 which provides digitized versions of both suitable for processing by processor 16 to display an image on display device 22.

Together, the acquisition electronics 12 provides the necessary hardware and software to collect a series of ultrasonic echo signals at a plurality of angles 14 through an imaged object 24, such as an organ. Two acquisitions are acquired at each angle 14 with different degrees of compression of the imaged object 24 in an axial direction by a compressor 26. Compression amounts are typically about 1% for tissue and may, for example, be an uncompressed and compressed state or two compressed states with different amounts of compression.

As used herein "axial" will be the direction that is parallel to the compressive force provided by compressor 26 along a z-axis and the term "orthogonal" will be used to describe either or both of a "lateral" direction perpendicular to the axial direction along an x-axis and "elevational" direction perpendicular to the axial and lateral direction along a y-axis. As will be understood from the following description the present invention is applicable to both lateral and elevational strains.

Under compression, the imaged object changes by decreasing in axial height by a decrease amount 27 and expanding laterally by expansion amount 28 determined generally by a Poisson's ratio for the material. The Poisson's ratio may allow for differentiation between normal and abnormal tissues. Further, for poroelastic materials, the Poisson's ratio may change during compression because of unbound liquids leaving the material, and thus imaging of Poisson's ratio may be used for quantitative assessment of fluid transport in regions of edema, inflammation, or the like.

Figure 2:
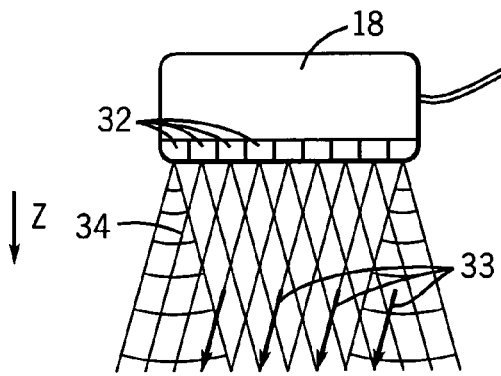
FIG. 2 is a front elevational view of a phased array transducer that may be part of the ultrasound machine of FIG. 1 to provide a steerable and focusable beam to obtain multi-angle measurements.

Referring now to FIG. 2 in a preferred embodiment, the transducer 18 is a multielement array transducer having multiple transmitting and receiving elements 32 such as may create independent wavefronts 34 as will be understood to those of ordinary skill in the art. A group of these elements is activated to create an individual ultrasound beam, and the beam's central axis is translated along the array to create an ultrasound image. Control of the phase of wavefronts of the elements 32 can provide for a steerable beam 33 that allows multiple angles of acoustic signals to be transmitted from and received by the transducer 18 without movement of the transducer 18. The central axes of these steered beams may also be translated along the array to create an angled image. Thus, signals from each voxel are obtained from a plurality of beam angles.

Figure 3:
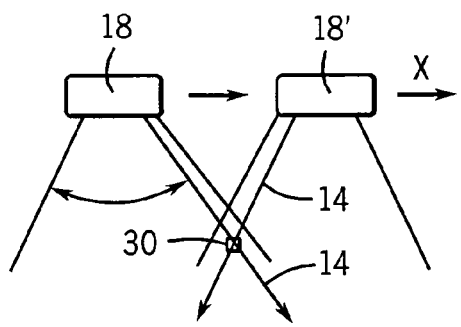
FIG. 3 is a view of the transducer of FIG. 2 as moved laterally in translation to provide for multi-angle measurements of a plurality of voxels.

Referring now to FIG. 3, moving the transducer 18 lateral direction (to a position denoted by transducer 18') allows individual voxels 30 to be measured at multiple angles 14 determined by the number of lateral movements and acquisitions. For example, each voxel may be measured by beams ranging from +45 to −45 degrees in one-degree or other fixed angular increments.

Figure 4:
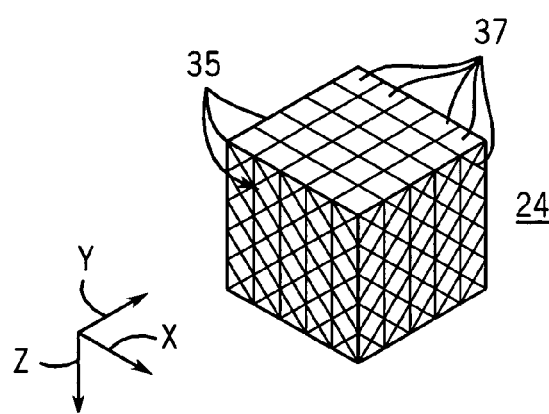
FIG. 4 is a simplified representation of three-dimensional ultrasonic measurements obtained by moving the transducer FIG. 2 both laterally and in elevation in two perpendicular sweeps to obtain multiple angled measurements in two perpendicular planes.

Referring now to FIG. 4, a set of scans with incremental lateral displacements along the x-axis may produce a scan plane 35 suitable for a two-dimensional analysis as will be described below. Moving the transducer 18 without rotation about the axial direction, after each scan plane 35 is acquired, allows the acquisition of multiple scan planes 25 covering a volume of the imaged object 24. In each of these scan planes 35, axial and lateral displacements can be determined. Rotation of the transducer 18 by 90° with incremental elevational displacements along the y-axis may produce a scan plane 37 perpendicular to scan planes 35. Moving the transducer 18 without rotation about the axial direction, after each scan plane 37 is acquired, allows the acquisition of multiple scan planes 37 covering the same volume of the imaged object 24 as the scan planes 35, but allowing axial and elevational displacements to be determined.

Instrumentation attached to the transducer 18 or analyses of the ultrasonic signals acquired during the scans may be used to provide an indication of the angle 14 and relative location of each acquired ultrasonic signal of the scan planes 35 and 37. Additional details with respect to an elastographic imaging machine suitable for programming per the present invention is described in co-pending U.S. application cited above.

Figure 5:
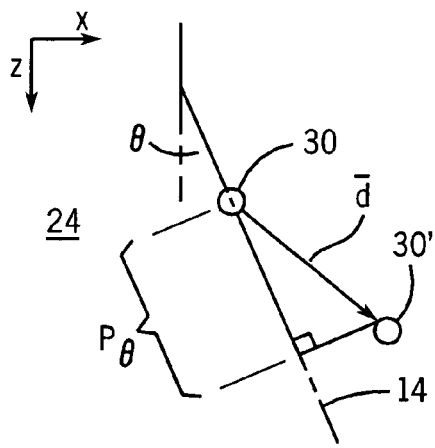
FIG. 5 is a geometric diagram of displacement of tissue in a voxel showing various quantities described in the present invention.

Referring now to FIG. 5, for each given voxel 30 within the imaged object 24 the axial compression will cause a displacement both in axial and orthogonal directions so that the volume element 30 under compression moves to a position denoted by volume element 30' typically having an axial or z-component portion $d_z$ and a lateral or elevational component $d_x$ or $d_y$. When this displacement denoted by vector $\bar{d}$ is measured along an angle 14 of one ultrasonic signal, only a projection of the displacement $\bar{d}$ will be detected by that angle 14. For small voxels 30, $\bar{d}$ may be approximated by a straight line and this projected displacement $q_\theta$ will be as follows:

$$q_\theta = d_z \cos\theta + d_x \sin\theta + n_0 \quad (1)$$

where $d_z$ and $d_x$ are axial and lateral components of the displacement vector $\bar{d}$ in the z- and x- directions, respectively, $\theta$ is the angle 14 with respect to the z axis, and $n_0$ is noise or inaccuracy in the measurement process. Minor modifications of equation (1) will provide the relationship for axial and elevational displacement. Note that this equation (1) does not require knowledge of Poisson's ratio or any other mechanical property of the imaged object 24 but is simply the result of geometric principles and is thus material independent.

Figure 6:
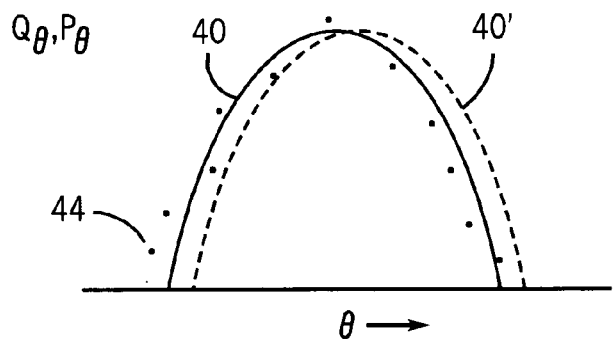
FIG. 6 is a plot showing two curves of a model of projected displacement for different displacements as a function of angle superimposed with measured data points.

Referring now to FIG. 6, a family of curves 40, 40' (only two are shown for clarity) may describe noiseless measurement of an arbitrary displacement vector $\bar{d}$ as a function of $\theta$. Each curve has a generally downward opening arc and the following the equation:

$$p_\theta = d_z \cos\theta + d_x \sin\theta \quad (2)$$

Generally as will not be described, in the present invention, for each voxel 30, measured data along the angles 14 is used to select one of these curves that best fits the measured data and this curve and its equation reveal an estimate of noiseless measurement of $d_z$ and $d_x$ (or $d_y$)

Figure 7:
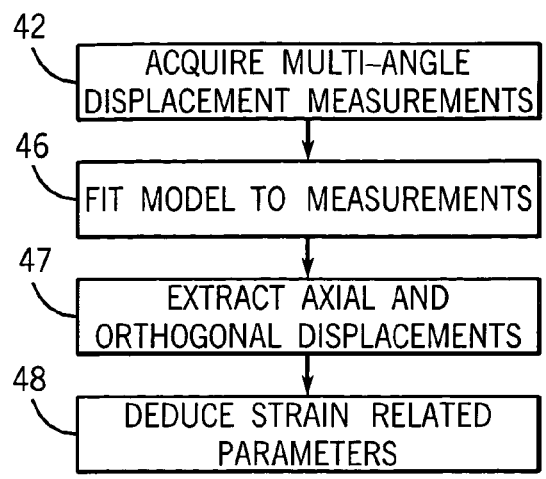
FIG. 7 is a flowchart showing steps of a program executed by a processor of the ultrasound machine of FIG. 1 in providing axial and orthogonal displacements for each voxel and parameters based on those displacements.

Referring to FIG. 7, in a first step of the present invention indicated by process block 42 such as may be implemented by software running on processor 16, a pair of ultrasonic signals $s_\theta$ and $s'_\theta$ are acquired along each of different unit vectors $u_\theta$ at angles $\theta$ during a multi-angle echo signal acquisition. Signal $s_\theta$ is obtained under a first state of tissue compression (e.g., no compression) and signal $s'_\theta$ is obtained with a predetermined compression.

These signals $s_\theta$ and $s'_\theta$ are processed according to standard elastographic techniques (for example, cross-correlation) to deduce a projected displacement $q_\theta$ at each voxel 30 for each angle $\theta$ per equation (1) above. Generally, the ultrasonic measurements along different angles 14 will not necessarily cross the center of the voxels 30 and accordingly interpolation may be applied to the displacements obtained at different angles 14 to bring them to a common point in the voxels 30.

Per process block 46, for each voxel 30, the measurements $q_\theta$ are fit to one of the family of curves providing values of $p_\theta$ that are closest to the values of $q_\theta$. While this may be done, for example, by iterating through combinations of $d_z$ and $d_x$ for the range of angles $\theta$, however, in the preferred embodiment, a least squares fit is rapidly obtained by using the following matrix relationship:

$$\bar{d} = (A^T A)^{-1} A^T \bar{q} \quad (3)$$

where:

$\bar{d}$ is the displacement vector $\begin{bmatrix} d_z \\ d_x \end{bmatrix}$ $\bar{q}$ is the set of measured projections of displacement $$\begin{bmatrix} q_{\theta_1} \\ q_{\theta_2} \\ \vdots \\ q_{\theta_m} \end{bmatrix} \text{ and } A = \begin{bmatrix} \cos\theta_1 & \sin\theta_1 \\ \cos\theta_2 & \sin\theta_2 \\ \vdots & \vdots \\ \cos\theta_m & \sin\theta_m \end{bmatrix}$$

The matrix product $A^T A$ is called the Grammian or Gram matrix and a solution exists for this equation (3) because the columns of A are linearly independent.

At process block 47 the axial and lateral displacements $d_z$ and $d_x$ are taken from the solution of equation (3) and then, as indicated at process block 48 used to deduce, for example, axial and lateral shear ($e_{zz}$, $e_{xx}$) being change in displacement as a function of the z or x axis, respectively, per the following equations (4) and (5):

$$e_{zz} = \frac{\partial d_z}{\partial z} \quad (4)$$

$$e_{xx} = \frac{\partial d_x}{\partial x} \quad (5)$$

In this case an assumption is made that the stress field is uniform, however, these equations may be easily modified as will be understood to one of ordinary skill in the art to accommodate varying stress fields.

From these quantities Poisson's ratio, shear strain ($e_{zx}$), and other parameters may be readily deduced as will be understood to those of ordinary skill in the art. Shear strain is given by the following equation:

$$e_{zx} = \frac{1}{2}\left(\frac{\partial d_z}{\partial x} + \frac{\partial d_x}{\partial z}\right) \quad (6)$$

Poisson's ratio may be determined for each voxel by division of the strain in the x direction and by the strains in the z direction recognizing that this method provides a good approximation only if the voxels are subject locally only to axial compression. Generally this will not be true around inclusions and therefore the present technique can be used to emphasize such features.

Each of these deduced parameters can be used to produce an image, for example, a Poisson's ratio image on display device 22.

It should be noted that the present invention does not preclude the use of other models than that provided by equations (1) and (2), including, for example, those that take into account other features of the measurement process. Note that the model may accommodate different numbers of ultrasonic measurements and accordingly will work even when the angles 14 along which measurements may be obtained are limited by structure.

Figure 8:
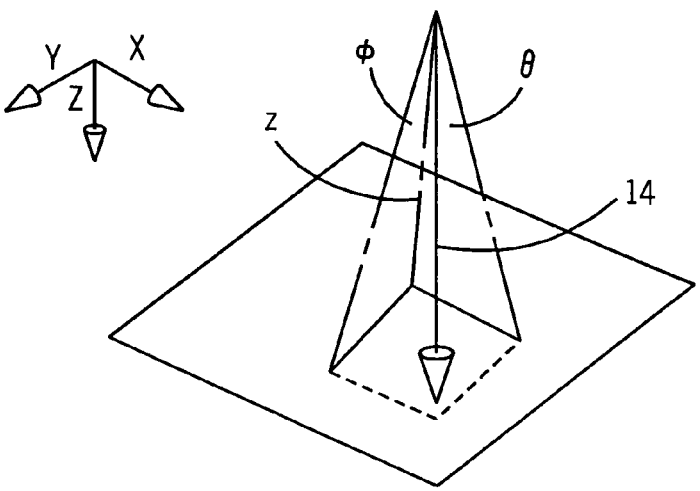
FIG. 8 is a geometric diagram showing quantities used in the extension of the techniques of FIGS. 5 and 6 to three dimensions.

Referring now to FIG. 8, the two dimensional models described above may be expanded to three dimensions by analyzing projected displacement $p_{\theta,\phi}$ as a function of both $\theta$ in a lateral plane and $\phi$ in an elevational plane perpendicular to the lateral plane as shown in FIG. 8. In this case curves 40 through 40' representing the modeling will be surfaces per the following equation:

$$p_{\theta,\phi} = d_z \cos\theta \cos\phi + d_x \sin\theta + d_y \cos\theta \sin\phi. \quad (7)$$

The fitting process takes measurements $q_{\theta,\phi}$ and fits them to one of these curves using equation (3) with the elements defined as follows:

$$\bar{q} = \begin{bmatrix} q_{\theta_1,\phi_1} \\ \vdots \\ q_{\theta_1,\phi_n} \\ q_{\theta_2,\phi_1} \\ \vdots \\ \vdots \\ q_{\theta_m,\phi_n} \end{bmatrix}$$

$$A = \begin{bmatrix} \cos\theta_1\sin\phi_1 & \sin\theta_1 & \cos\theta_1\sin\phi_1 \\ \vdots & \vdots & \vdots \\ \cos\theta_1\sin\phi_n & \sin\theta_1 & \cos\theta_1\sin\phi_n \\ \cos\theta_2\sin\phi_1 & \sin\theta_2 & \cos\theta_2\sin\phi_1 \\ \vdots & \vdots & \vdots \\ \vdots & \vdots & \vdots \\ \cos\theta_m\sin\phi_n & \sin\theta_m & \cos\theta_m\sin\phi_n \end{bmatrix}$$

$$\bar{d} = \begin{bmatrix} d_z \\ d_x \\ d_y \end{bmatrix}$$

It will be apparent from this description to one of ordinary skill in the art that a number of variations may be made in the preferred embodiment that will still be within the spirit and scope of the claims. For example, while the preferred embodiment contemplates ultrasonic echo signals, the present invention can also be used with through transmitted ultrasonic waves. The invention contemplates use with alternative ultrasonic transducer technology and other methods of obtaining multiple angles of ultrasonic measurements through the voxels of the imaged object 24 including area array transducers providing cone beams that may be phased to sweep through angles over three dimensions or individual ultrasonic transducers that may be moved in translation and rotation to acquire the necessary data.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ultrasonic elastography system comprising:
   a graphic display;
   an ultrasonic acquisition assembly adapted to provide a set of ultrasonic signals from a plurality of voxels in a region of interest at a plurality of angles through the voxels, the set of ultrasonic signals including a first subset of ultrasonic signals taken with tissue of the region of interest in a first axial compressive state and a corresponding second subset of ultrasonic signals taken with tissue of the region of interest in a second axial compressive state; and
   a processor receiving the set of ultrasonic signals and executing a stored program to:
   (i) measure the displacement of each voxel projected along the angle of each of the ultrasonic signals between the first and second compressive states;
   (ii) analyze the measured displacements at multiple angles for each voxel to determine a displacement for the voxel along a predetermined angle; and
   (iii) display a graphic representation of the elasticity of the tissue based on displacement of the voxel along the predetermined angle.

2. The ultrasonic elastography system of claim 1 wherein the electronic computer analyzes the measured displacements at multiple angles for each voxel to determine an axial and orthogonal displacement for the voxel.

3. The ultrasonic elastography system of claim 2 wherein the analysis of the displacement estimates axial and orthogonal displacements by fitting a model to the measured displacements, the model relating projected angular displacement to axial and orthogonal displacement.

4. The ultrasonic elastography system of claim 3 wherein the model does not presuppose material properties of the voxels.

5. The ultrasonic elastography system of claim 3 wherein the model provides a geometric decomposition of displacement measured along angles into projections along axial and orthogonal axes.

6. The ultrasonic elastography system of claim 3 wherein the model is:

$$p_\theta = d_z \cos\theta + d_x \sin\theta$$

where:
   $p_\theta$ is a model predicted projection of the displacement along the angle of the ultrasonic signal:
   $d_z$ and $d_x$ are axial and orthogonal displacements, respectively, producing the projected displacement;
   wherein the fitting process matches the model predicted projections to measure displacements $q_\theta$ for each angle of measurement $\theta$.

7. The ultrasonic elastography system of claim 6 wherein the fitting process is a least squares fit solving the following equation:

$$\bar{d} = (A^T A)^{-1} A^T \bar{q}$$

where:

$\vec{d}$ is the displacement vector $\begin{bmatrix} d_z \\ d_x \end{bmatrix}$;

$\vec{q}$ is the set of measured projections of displacement $\begin{bmatrix} q_{\theta_1} \\ q_{\theta_2} \\ \vdots \\ q_{\theta_m} \end{bmatrix}$; and $A = \begin{bmatrix} \cos\theta_1 & \sin\theta_1 \\ \cos\theta_2 & \sin\theta_2 \\ \vdots & \vdots \\ \cos\theta_m & \sin\theta_m \end{bmatrix}$.

8. The ultrasonic elastography system of claim 2 wherein the processor further executes the stored program to determine parameters for the voxels related to the determined axial and orthogonal displacements.

9. The ultrasonic elastography system of claim 8 wherein a parameter related to the determined axial and orthogonal displacements is Poisson's ratio.

10. The ultrasonic elastography system of claim 8 wherein a parameter related to the determined axial and orthogonal displacements is shear strain.

11. The ultrasonic elastography system of claim 2 wherein the determined parameters are axial and orthogonal strains.

12. The ultrasonic elastography system of claim 2 wherein the orthogonal displacement is selected from at least one of the group consisting of: lateral displacement and elevational displacement.

13. The ultrasonic elastography system of claim 2 further including a display device and wherein the processor provides an image output based on the determined axial and orthogonal displacements.

14. The ultrasonic elastography system of claim 13 wherein the image output is selected from a group of: images of axial and lateral strain, images of voxel Poisson's ratio, and images of shear strain.

15. The ultrasonic elastography system of claim 1 wherein one compressive state is no compression.

16. The ultrasonic elastography method of claim 1 wherein both the first and second compressive states are states of absolute compression.

17. The ultrasonic elastography system of claim 1 wherein the plurality of angles of ultrasonic signals are in multiple perpendicular planes.

18. The ultrasonic elastography system of claim 1 wherein the ultrasonic acquisition assembly includes a transducer selected from the group consisting of: a single transducer element moved in location and angle, a multi-element transducer moved in location and angle, and a phased array transducer sweeping in angle and moved in location, and a multielement transducer with beam-steering.

19. A method of ultrasonic elastography of tissue comprising the steps of:

(a) acquiring a set of ultrasonic signals from a plurality of voxels in a region of interest of the tissue at a plurality of angles through the voxels, the set of ultrasonic signals including a first subset of ultrasonic signals taken with the tissue of the region of interest in a first axial compressive state and a corresponding second subset of ultrasonic signals taken with tissue of the region of interest in a second axial compressive state;

(b) measuring the displacement of each voxel projected along the angle of each of the ultrasonic signals between the first and second compressive states;

(c) fitting a model providing projected displacement as a function of ultrasonic signal angle and axial and orthogonal displacement to the measured displacements;

(d) determining axial and orthogonal displacement for the voxels from the fit model; and (e) displaying elasticity of the tissue based on the determined axial and orthogonal displacement.

20. The ultrasonic elastography method of claim 19 including the further step of determining parameters for the voxels related to the determined axial and orthogonal displacement.

21. The ultrasonic elastography method of claim 20 wherein a parameter related to the determined axial and orthogonal displacement is Poisson's ratio.

22. The ultrasonic elastography method of claim 20 wherein a parameter related to the determined axial and orthogonal displacement is shear strain.

23. The ultrasonic elastography method of claim 19 wherein the orthogonal displacement is selected from at least one of the group consisting of: lateral displacement and elevational displacement.

24. The ultrasonic elastography method of claim 19 wherein the model does not presuppose material properties of the voxels.

25. The ultrasonic elastography method of claim 19 wherein the model provides a geometric decomposition of displacement measured along angles into projections along axial and orthogonal axes.

26. The ultrasonic elastography method of claim 19 wherein the model is:

$$p_\theta = d_z \cos\theta + d_x \sin\theta$$

where:

$p_\theta$ is a model predicted projection of the displacement along the angle of the ultrasonic signal;

$d_z$ and $d_x$ are axial and orthogonal displacements, respectively, producing the projected displacement;

wherein the fitting process matches the model predicted projections to measure displacements $q_\theta$ for each angle of measurement $\theta$.

27. The ultrasonic elastography method of claim 26 wherein the fitting process is a least squares fit solving the following equation:

$$\vec{d} = (A^T A)^{-1} A^T \vec{q}$$

where:

$\vec{d}$ is the displacement vector $\begin{bmatrix} d_z \\ d_x \end{bmatrix}$;

$\vec{q}$ is the set of measured projections of displacement $\begin{bmatrix} q_{\theta_1} \\ q_{\theta_2} \\ \vdots \\ q_{\theta_m} \end{bmatrix}$; and $A = \begin{bmatrix} \cos\theta_1 & \sin\theta_1 \\ \cos\theta_2 & \sin\theta_2 \\ \vdots & \vdots \\ \cos\theta_m & \sin\theta_m \end{bmatrix}$.

28. The ultrasonic elastography method of claim 19 wherein one compressive state is no compression.

29. The ultrasonic elastography method of claim 19 wherein both the first and second compressive states are states of absolute compression.

30. The ultrasonic elastography method of claim 19 wherein the plurality of angles of ultrasonic signals are in multiple perpendicular planes.

31. The ultrasonic elastography method of claim 19 including the step of providing an image output based on the determined axial and orthogonal displacements.

32. The ultrasonic elastography method of claim 19 wherein the image output is selected from a group of: images of axial, lateral and elevational strain, images of voxel Poisson's ratio, and images of shear strain.

* * * * *

UNITED STATES PATENT AND TRADEMARK OFFICE
CERTIFICATE OF CORRECTION

PATENT NO.         : 7,331,926 B2
APPLICATION NO.    : 10/784526
DATED              : February 19, 2008
INVENTOR(S)        : Tomy Varghese It is certified that error appears in the above-identified patent and that said Letters Patent is hereby corrected as shown below:

IN THE SPECIFICATION

Column 1, line 14, please amend the paragraph as follows:

-- This invention was made with ~~United States~~ government support under CA086278 awarded by the ~~following agencies: NIH CA86278~~ National Institutes of Health. The ~~United States~~ government has certain rights ~~to this~~ in the invention. --

Signed and Sealed this
Seventh Day of May, 2013

Teresa Stanek Rea
*Acting Director of the United States Patent and Trademark Office*